(12) United States Patent
Bronte-Stewart et al.

(10) Patent No.: US 12,740,740 B2
(45) Date of Patent: Sep. 22, 2026

(54) SYSTEMS AND METHODS FOR DIGITOGRAPHIC MEASUREMENT OF PARKINSON'S DISEASE

(71) Applicant: The Board of Trustees of the Leland Stanford Junior University, Stanford, CA (US)

(72) Inventors: Helen Bronte-Stewart, Pacifica, CA (US); Megan H. Trager, Saratoga, CA (US); Simon Revlock, Encinitas, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 723 days.

(21) Appl. No.: 18/018,547

(22) PCT Filed: Jul. 29, 2021

(86) PCT No.: PCT/US2021/043787
§ 371 (c)(1),
(2) Date: Jan. 27, 2023

(87) PCT Pub. No.: WO2022/026765
PCT Pub. Date: Feb. 3, 2022

(65) Prior Publication Data

US 2024/0008798 A1 Jan. 11, 2024

Related U.S. Application Data

(60) Provisional application No. 63/058,426, filed on Jul. 29, 2020.

(51) Int. Cl.
*A61B 5/00* (2006.01)
*A61B 5/11* (2006.01)

(52) U.S. Cl.
CPC .......... *A61B 5/4082* (2013.01); *A61B 5/1124* (2013.01); *A61B 5/7475* (2013.01)

(58) Field of Classification Search
CPC ... A61B 5/4082; A61B 5/1124; A61B 5/7475; A61B 2090/064; A61B 5/743
(Continued)

(56) References Cited

U.S. PATENT DOCUMENTS

| | | | | |
|---|---|---|---|---|
| 6,416,485 B1 * | 7/2002 | Rovetta | A61B 5/162 600/595 |
| 10,506,979 B2 | 12/2019 | Giancardo et al. | |

(Continued)

FOREIGN PATENT DOCUMENTS

| | | | |
|---|---|---|---|
| EP | 2659835 A1 * | 11/2013 | A61B 5/225 |
| EP | 4188203 A1 | 6/2023 | |

(Continued)

OTHER PUBLICATIONS

International Preliminary Report on Patentability for International Application PCT/US2021/043787, Report issued Jan. 31, 2023, Mailed on Feb. 9, 2023, 11 Pgs.

(Continued)

*Primary Examiner* — Jacqueline Cheng
*Assistant Examiner* — Jonathan E. Cooper
(74) *Attorney, Agent, or Firm* — KPPB LLP

(57) ABSTRACT

Systems and methods for digitographic measurement of Parkinson's disease in accordance with embodiments of the invention are illustrated. One embodiment includes a digitographic measurement device, including a housing, a plurality of keys attached to the housing, a plurality of sensors, sensor in the plurality of sensors is associated with a key in the plurality of keys and is capable of measuring the amplitude of a key press, and an input/output interface within the housing, where the digitographic measurement (Continued)

device is configured to transmit key press data generated by the sensors to a controller via the input/output interface, and where the key press data is used to generate a plurality of digitographic metrics that describe motor symptoms of a user of the digitographic measurement device.

19 Claims, 8 Drawing Sheets

(58) Field of Classification Search
USPC .......................................................... 600/595
See application file for complete search history.

(56) References Cited

U.S. PATENT DOCUMENTS

| | | | | |
|---|---|---|---|---|
| 2010/0106060 | A1 | 4/2010 | Tsuji et al. | |
| 2011/0054361 | A1* | 3/2011 | Sakoda | A61B 5/4082 600/595 |
| 2011/0098608 | A1* | 4/2011 | Griffiths | A61B 5/4082 600/595 |
| 2011/0267042 | A1 | 11/2011 | Sano et al. | |
| 2015/0272504 | A1 | 10/2015 | Giancardo et al. | |
| 2018/0126219 | A1* | 5/2018 | Parvaneh | G16H 40/63 |
| 2019/0200915 | A1* | 7/2019 | Baker | A61B 5/4839 |
| 2019/0380625 | A1* | 12/2019 | Lindberg | A61B 5/1125 |
| 2020/0089286 | A1 | 3/2020 | Weldon et al. | |
| 2021/0236044 | A1* | 8/2021 | Arroyo-Gallego | A61B 5/112 |

FOREIGN PATENT DOCUMENTS

| | | | | | |
|---|---|---|---|---|---|
| JP | S54133389 | U | | 9/1979 | |
| JP | H0749688 | A | | 2/1995 | |
| JP | 2010099263 | A | | 5/2010 | |
| JP | 2011004840 | A | * | 1/2011 | A61B 5/11 |
| JP | 2021500183 | A | | 1/2021 | |
| JP | 2023536464 | A | | 8/2023 | |
| WO | WO-9739677 | A1 | * | 10/1997 | A61B 5/1101 |
| WO | WO-2009144325 | A1 | * | 12/2009 | G06Q 50/22 |
| WO | 2019081640 | A2 | | 5/2019 | |
| WO | 2022026765 | A1 | | 2/2022 | |

OTHER PUBLICATIONS

International Search Report and Written Opinion for International Application No. PCT/US2021/043787, Search completed Oct. 1, 2021, Mailed on Nov. 1, 2021, 17 Pgs.

Agostino et al., "Clinical impairment of sequential finger movements in Parkinson's disease", Movement Disorders, vol. 13, No. 3, May 1998, pp. 418-421, doi: 10.1002/mds.870130308.

Arroyo-Gallego et al., "Detecting Motor Impairment in Early Parkinson's Disease via Natural Typing Interaction With Keyboards: Validation of the neuroQWERTY Approach in an Uncontrolled At-Home Setting", Journal of Medical Internet Research, vol. 20, No. 3, Mar. 2018, 24 pgs.

Benecke et al., "Motor strategies involved in the performance of sequential movements", Experimental Brain Research, vol. 63, No. 3, 1986, pp. 585-595, doi: 10.1007/BF00237481.

Brocker et al., "Improved Efficacy of Temporally Non-Regular Deep Brain Stimulation in Parkinson's Disease", Experimental Neurology, vol. 239, Jan. 2013, pp. 60-67, DOI: 10.1016/j.expneurol.2012.09.008.

Bronte-Stewart et al., "Quantitative Digitography (QDG): A Sensitive Measure of Digital Moto Control in Idiopathic Parkinson's Disease", Movement Disorders, vol. 15, No. 1, 2000, pp. 36-47.

Fereshtehnejad et al., "Evolution of prodromal Parkinson's disease and dementia with Lewy bodies: a prospective study", Brain, No. 142, 2019, pp. 2051-2067, DOI: 10.1093/brain/awz155.

Goetz et al., "Movement Disorder Society-sponsored revision of the Unified Parkinson's Disease Rating Scale (MDS-UPDRS): scale presentation and clinimetric testing results", Movement Disorders, vol. 23, Issue 15, Nov. 2008, pp. 2109-2266.

Goetz et al., "Testing objective measures of motor impairment in early Parkinson's disease: feasibility study of an at-home testing device", Movement Disorders, vol. 24, No. 4, Mar. 15, 2009, pp. 551-556, doi: 10.002/mds.22379.

Hely et al., "Reliability of the Columbia scale for assessing signs of Parkinson's disease", Movement Disorders, vol. 8, No. 4, 1993, pp. 466-472.

Louie et al., "Quantitative Lateralized Measures of Bradykinesia at Different Stages of Parkinson's Disease: The Role of the Less Affected Side", Movement Disorders, vol. 24, No. 13, 2009, pp. 1991-1997.

Marsden et al., "The functions of the basal ganglia and the paradox of stereotaxic surgery in Parkinson's disease", Brain, vol. 117, Issue 4, Aug. 1994, pp. 877-897, doi: 10.1093/brain/117.4.877.

Miller Koop et al., "Quantitative Measures of Fine Motor, Limb, and Postural Bradykinesia in Very Early Stage, Untreated Parkinson's Disease", Movement Disorders, vol. 23, No. 9, 2008, pp. 1262-1268.

Nantel et al., "Repetitive stepping in place identifies and measures freezing episodes in subjects with Parkinson's disease", Gait & Posture, vol. 34, 2011, pp. 329-333.

Prabhakar et al., "Quantitative Digitography Measures Fine Motor Disturbances in Chronically Treated HIV Similar to Parkinson's Disease", Frontiers in Aging Neuroscience, vol. 12, No. 539598, Oct. 2020, DOI: 10.3389/fnagi.2020.539598.

Tavares et al., "Quantitative Measurements of Alternating Finger Tapping in Parkinson's Disease Correlate with UPDRS Motor Disability and Reveal the Improvement in Fine Motor Control From Medication and Deep Brain Stimulation", Movement Disorders, vol. 20, No. 10, 2005, pp. 1286-1298.

Trager et al., "A validated measure of rigidity in Parkinson's disease using alternating finger tapping on an engineered keyboard", Parkinsonism and Related Disorders, vol. 81, 2020, pp. 161-164.

Trager et al., "Arrhythmokinesis is evident during unimanual not bimanual finger tapping in Parkinson's disease", Journal of Clinical Movement Disorders, vol. 2, No. 8, 2015, 7 pgs., doi: 10.1186s40734-015-0019-2.

Extended European Search Report for European Application No. 21850510.5, Search completed Jun. 14, 2024, Mailed Jul. 1, 2024, 8pgs.

* cited by examiner

SYSTEMS AND METHODS FOR DIGITOGRAPHIC MEASUREMENT OF PARKINSON'S DISEASE

CROSS-REFERENCE TO RELATED APPLICATIONS

The current application is a U.S. national stage of PCT Patent Application No. PCT/US2021/043787 titled "Systems and Methods for Digitographic Measurement of Parkinson's Disease", filed Jul. 29, 2021, which claims the benefit of U.S. Provisional Patent Application No. 63/058,426 titled "Systems and Methods for Objective Parkinson's Disease Rigidity Measurements", filed Jul. 29, 2020. The disclosures of PCT Patent Application No. PCT/US2021/043787 and U.S. Provisional Patent Application No. 63/058,426 is hereby incorporated by reference in their entirety.

FIELD OF THE INVENTION

The present invention generally relates to systems and methods for recording and analyzing digitographic measurements of patients, and providing possible diagnoses based on said measurements.

BACKGROUND

Parkinson's disease (PD) is a long-term degenerative nervous system disorder that affects the motor system, along with many other systems. Currently, there is no cure for PD. Diagnosis of PD relies upon two of three cardinal motor signs of PD: rigidity, bradykinesia, and/or resting tremor. There is currently no known biomarker for PD.

SUMMARY OF THE INVENTION

Systems and methods for digitographic measurement of Parkinson's disease in accordance with embodiments of the invention are illustrated. One embodiment includes a digitographic measurement device, including a housing, a plurality of keys attached to the housing, a plurality of sensors, sensor in the plurality of sensors is associated with a key in the plurality of keys and is capable of measuring the amplitude of a key press, and an input/output interface within the housing, where the digitographic measurement device is configured to transmit key press data generated by the sensors to a controller via the input/output interface, and where the key press data is used to generate a plurality of digitographic metrics that describe motor symptoms of a user of the digitographic measurement device.

In another embodiment, each key in the plurality of keys is tensioned by a spring, and wherein the material of each key and tension of the spring minimizes bounce when the key is released.

In a further embodiment, at least one sensor in the plurality of sensors is selected from the group consisting of Hall effect sensors, optical sensors, magnetic encoders, and potentiometers.

In still another embodiment, the digitographic metrics at least one of: a rigidity metric, a bradykinetic amplitude metric, a bradykinetic frequency metric, a bradykinetic sequence effect metric, a tremor metric, a freeze behavior metric, and a freezing of upper limb (FOUL) metric.

In a still further embodiment, the rigidity metric is calculated by averaging difference in amplitude between a lowest point of a given key press and a highest point of a given key release subsequent to the given key press, for each key press in the key press data.

In yet another embodiment, the bradykinetic amplitude metric is calculated by averaging the distance between a highest point of a given key press and a lowest point of a subsequent key press, for each key press in the key press data.

In a yet further embodiment, the bradykinetic frequency metric is calculated by taking the inverse of the mean of the interstrike interval over the key press data.

In another additional embodiment, the bradykinetic sequence effect metric is calculated by fitting at least one exponential curve to quantify a decrement in amplitude over time.

In a further additional embodiment, the tremor metric is calculated as the percentage of time over the key press data where an interstrike interval between two consecutive key presses is less than 200 ms and the duration of at least one of the two consecutive key presses is less than 70 ms.

In another embodiment again, the freeze behavior metric is the coefficient of variation of an interstrike interval.

In a further embodiment again, the FOUL metric is calculated as the percentage of time over the key press data where an interstrike interval between two consecutive key presses is greater than a mean interstrike interval over preceding key presses plus two standard deviations.

In still yet another embodiment, a digitographic metric outside of a respective normative range indicates presence of a motor symptom.

In a still yet further embodiment, the key press data is further used to generate a report indicating the presence of Parkinson's disease based on digitographic metric values indicating the presence of at least two cardinal motor symptoms of Parkinson's disease.

In still another additional embodiment, the controller is integrated into the housing.

In a still further additional embodiment, a method for diagnosing motor symptoms, includes providing a digitographic measurement device to a user, performing a rapid alternating finger tapping (RAFT) test using the digitographic measurement device, recording key press data describing the amplitude of each key over the course of the RAFT test, calculating a plurality of digitographic metrics based on the key press data, and providing the digitographic metrics and an indication of which motor symptoms the user presents based on the digitographic metrics.

In still another embodiment again, the digitographic metrics at least one of: a rigidity metric, a bradykinetic amplitude metric, a bradykinetic frequency metric, a bradykinetic sequence effect metric, a tremor metric, a freeze behavior metric, and a freezing of upper limb (FOUL) metric.

In a still further embodiment again, the method further includes providing an indication that the user presents with Parkinson's disease when the digitographic metrics indicate the presence of at least two cardinal motor symptoms of Parkinson's disease.

In yet another additional embodiment, the digitographic measurement device includes a housing, a plurality of keys attached to the housing, a plurality of sensors, sensor in the plurality of sensors is associated with a key in the plurality of keys and is capable of measuring the amplitude of a key press, and an input/output interface within the housing.

In a yet further additional embodiment, a digitographic measurement system for measuring motor symptoms, includes a digitographic measurement device, including a housing, a plurality of keys attached to the housing, a plurality of sensors, sensor in the plurality of sensors is associated with a key in the plurality of keys and is capable of measuring the amplitude of a key press, and an input/output interface within the housing, where the digitographic measurement device is configured to transmit key press data generated by the sensors to a controller via the input/output interface, the controller, including a processor, and a memory containing a digitographic measurement application, where the digitographic measurement application directs the processor to obtain the key press data from the digitographic measurement device, calculate a plurality of digitographic metrics that describe motor symptoms of a user of the digitographic measurement device, and provide a report comprising the plurality of digitographic metrics and an indication of the presence of any motor symptoms in a user based on the plurality of digitographic metrics.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Figure 1A:
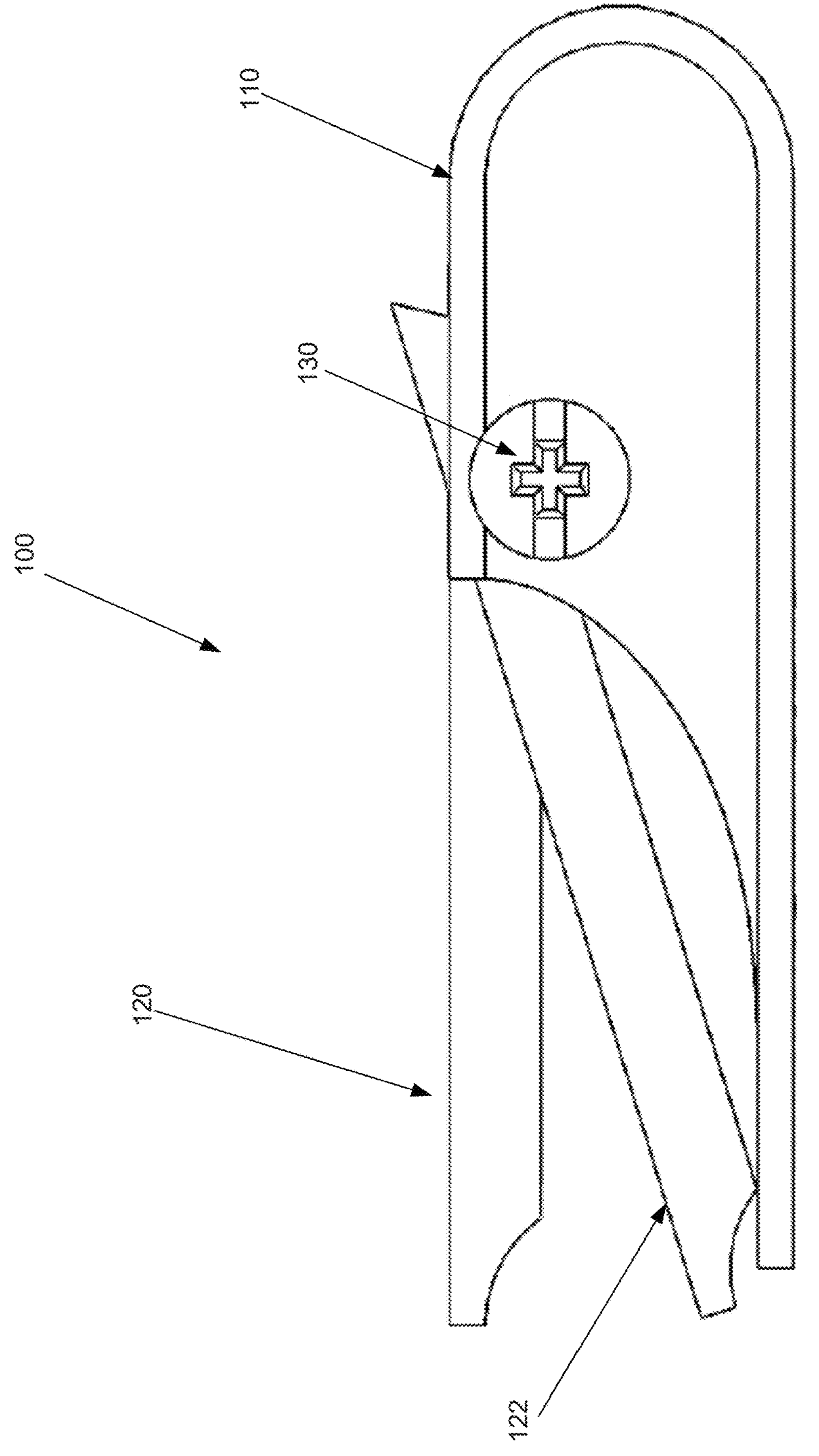
FIG. 1A is a side view of a digitographic measurement device in accordance with an embodiment of the invention.

Turning now to the drawings, systems and methods for digitographic measurement of Parkinson's disease are illustrated. Presently, Parkinson's disease is diagnosed when a patient presents at least two of three cardinal motor signs: rigidity, bradykinesia, and resting tremor. Tests for these signs are conventionally performed by trained medical specialists using a clinical rating scale such as the Movement Disorders Society's Unified Parkinson's Disease Rating Scale (MDS-UPDRS) part III (motor scale). As assessment is typically performed by human professionals, even when using a "gold standard" like the MDS-UPDRS, there is room for error. For example, the testing procedure is subjective and there is significant unreliability between different professionals despite certification procedures. Further, rigidity cannot presently be assessed visually, impeding the ability to generate consensus amongst non-present medical professionals (e.g. by video). This poses serious issues with respect to telemedicine which has become increasingly important to public health.

Quantitative digitography (QDG) has been proposed as a method for objectively measuring Parkinsonian motor symptoms. In particular, the kinematics of repetitive alternating finger-tapping (RAFT) has been shown to correlate with MDS-UPDRS motor scores. However, conventional QDG-RAFT analysis presents a number of issues which precludes wide-spread adoption. For example, accuracy in measurements and their relation to Parkinson's can differ between recording devices, traditionally MIDI piano keyboards. Such keyboards fail to provide a complete suite of data such as (but not limited to) amplitude metrics, and therefore produce lower quality results. Further, relationships between the acquired signals and Parkinson's have not been fully understood. Systems and methods described herein address the issues with conventional QDG-RAFT, and provide a replicable system and methodology by which Parkinson's can be reliably diagnosed.

In many embodiments, systems and methods described herein utilize a digitographic measurement device which precisely measures key displacement over time. In various embodiments, digitographic measurement devices have two keys, each with known displacement distances, key lengths, and key stiffnesses. Keys can include indents to ensure nearly identical finger placement across tests. Data from digitographic measurement devices can be used by controllers to provide an indication of which and how many cardinal motor symptoms a user presents, often when the patient is very early in the progression of the disease. Digitographic measurement devices are described in further detail below.

Digitographic Measurement Devices

Digitographic measurement devices are capable of recording various metrics regarding key presses as key press data. In many embodiments, digitographic measurement devices include two keys, as well as a sensor suite for measuring the depression of each key independently and continuously. In various embodiments, digitographic measurement devices record the amplitude of a key press, i.e. how far a key has been depressed relative to its resting position. In many embodiments, a continuous time signal measuring the offset from the rest position for each key makes up key press data. While many digitographic measurement devices include two keys, any number of keys can be used as appropriate to the requirements of specific applications of embodiments of the invention. For example, a digitographic measurement device utilizing 4 keys can be used to measure both right- and left-hand tasks at the same time instead of using two separate, two keyed devices. Similarly, if all fingers at once for one hand (5 keys) or both hands (10 keys) are to be tested, the digitographic measurement devices can be constructed to match these requirements without departing from the scope or spirit of the invention. Indeed, as can be readily appreciated, any arbitrary number of keys can be utilized.

Figures 1B, 1C:
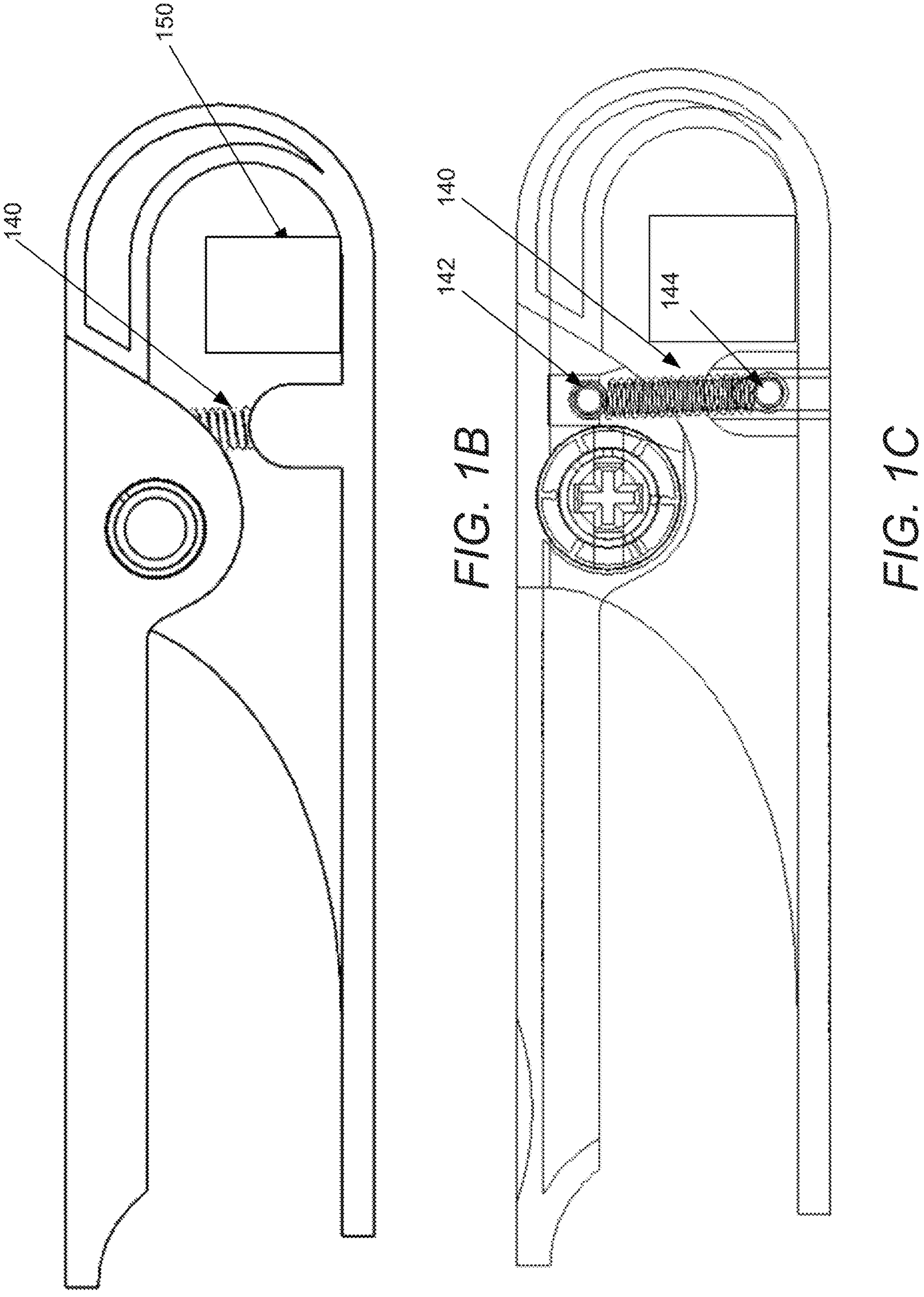
FIG. 1B is a first cross-sectional side view of a digitographic measurement device in accordance with an embodiment of the invention.
FIG. 1C is a second cross-sectional side view of a digitographic measurement device in accordance with an embodiment of the invention.

Turning now to FIG. 1A-D, an example digitographic measurement device in accordance with an embodiment of the invention is illustrated. FIG. 1A illustrates a side view of a digitographic measurement device 100. The device 100 has a housing 100 which supports two keys 120 and 122 (with key 122 illustrated as being fully depressed in FIG. 1A). The keys 120 and 122 pivot on an axel 130. FIG. 1B illustrates a first cross sectional side view of device 100, whereby spring 140 can be seen tensioning a key. In many embodiments, each key is tensioned by a respective spring. In many embodiments, the keys are resistant to deforming under pressure, and the spring tension is set to minimize bounce when the key is released. In this way, passive release of a key is minimally impacted by force from the key striking the bottom of the device. FIG. 1C illustrates a second cross-sectional side view of device 100 providing additional detail regarding connection of spring 140 to the key at connection point 142 and to the housing at connection point 144. The housing also holds an electronics package 150 which contains sensors and/or communications circuitry. In many embodiments, each key is associated with its own sensor.

Digitographic measurement devices can include one or more sensors capable of continuously measuring key press amplitudes. In numerous embodiments, Hall effect sensors are used to measure key displacement from the resting position. However, other sensing methodologies such as (but not limited to) optical sensors, magnetic encoders, and potentiometers can be used as long as they accurately measure key displacement as appropriate to the requirements of specific applications of embodiments of the invention. Depending on the type of sensor and particular construction of the digitographic measurement device, the sensors may be in different locations.

Figure 1D:
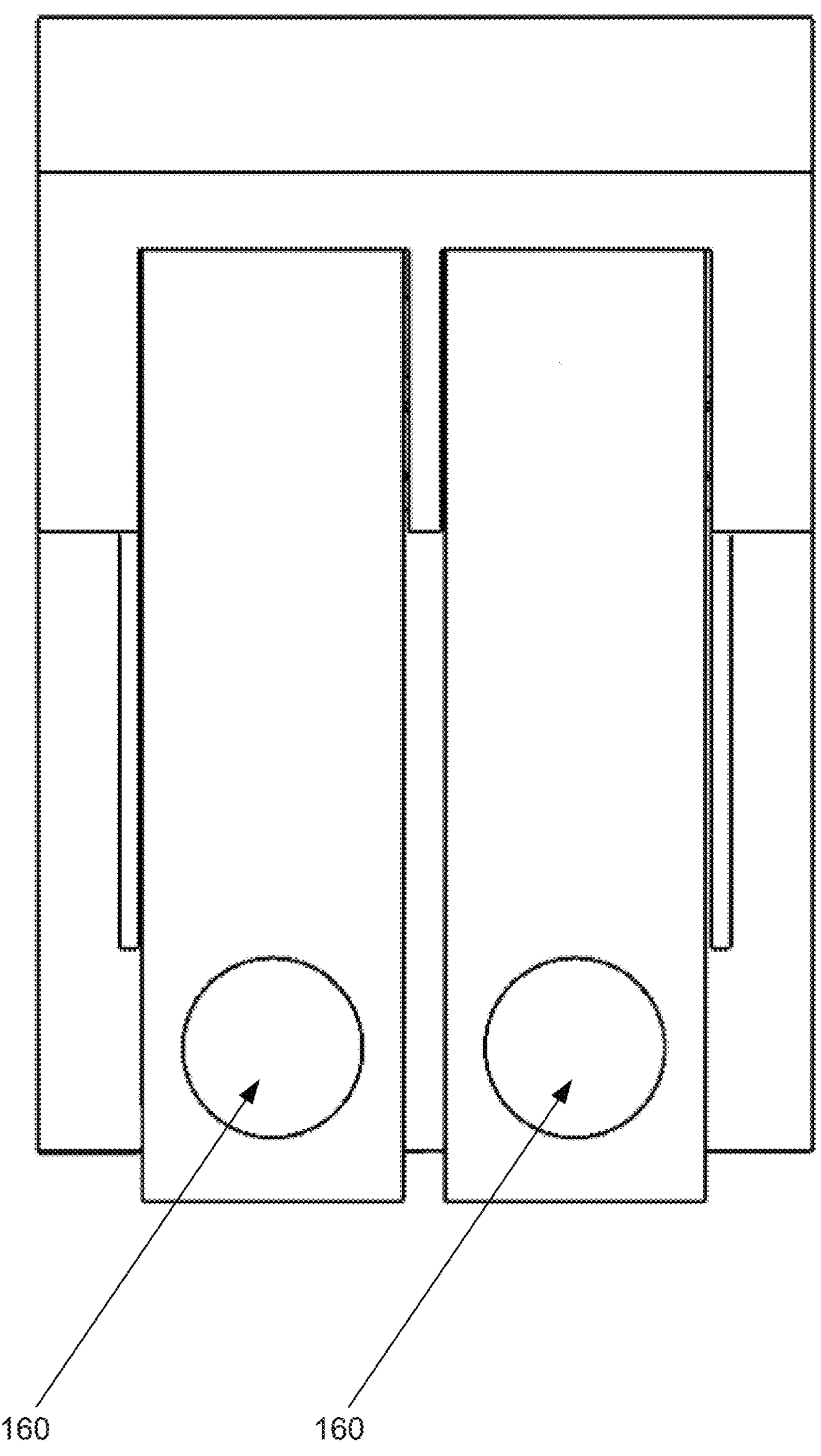
FIG. 1D is a top view of a digitographic measurement device in accordance with an embodiment of the invention.

A communications interface can be included in the electronics package capable of transmitting key press data. In many embodiments, the communications interface is capable of wirelessly transmitting key press data. For example, in various embodiments, a radio frequency communications device can be incorporated capable of communicating using any number of different wireless communications methodologies including (but not limited to) Bluetooth, Wi-Fi, and/or any other wireless communications methodology as appropriate to the requirements of specific applications of embodiments of the invention. As can be readily appreciated, additional wireless communications methodologies can be used that do not use radio frequency, such as (but not limited to) near-field magnetic induction communication and/or infrared communication. Various embodiments utilize wired communication to transmit key press data, either alone or in addition to wireless communication. While a particular electronics package 150 is illustrated in FIGS. 1B and 1C, it is to be understood that the communications interface and the sensors may be in different locations, and in fact may respectively be in different locations depending on the construction of the digitographic measurement device as appropriate to the requirements of specific applications of embodiments of the invention. Key press data can be processed by controllers as part of a digitographic measurement system. A top down video of the digitographic measurement device 100 is illustrated in FIG. 1D. As can be seen divots 160 can be included on the keys in order to provide a guidepost for users to standardize their finger positioning over multiple tests. Such systems are described in further detail below.

Digitographic Measurement Systems

Figure 2:
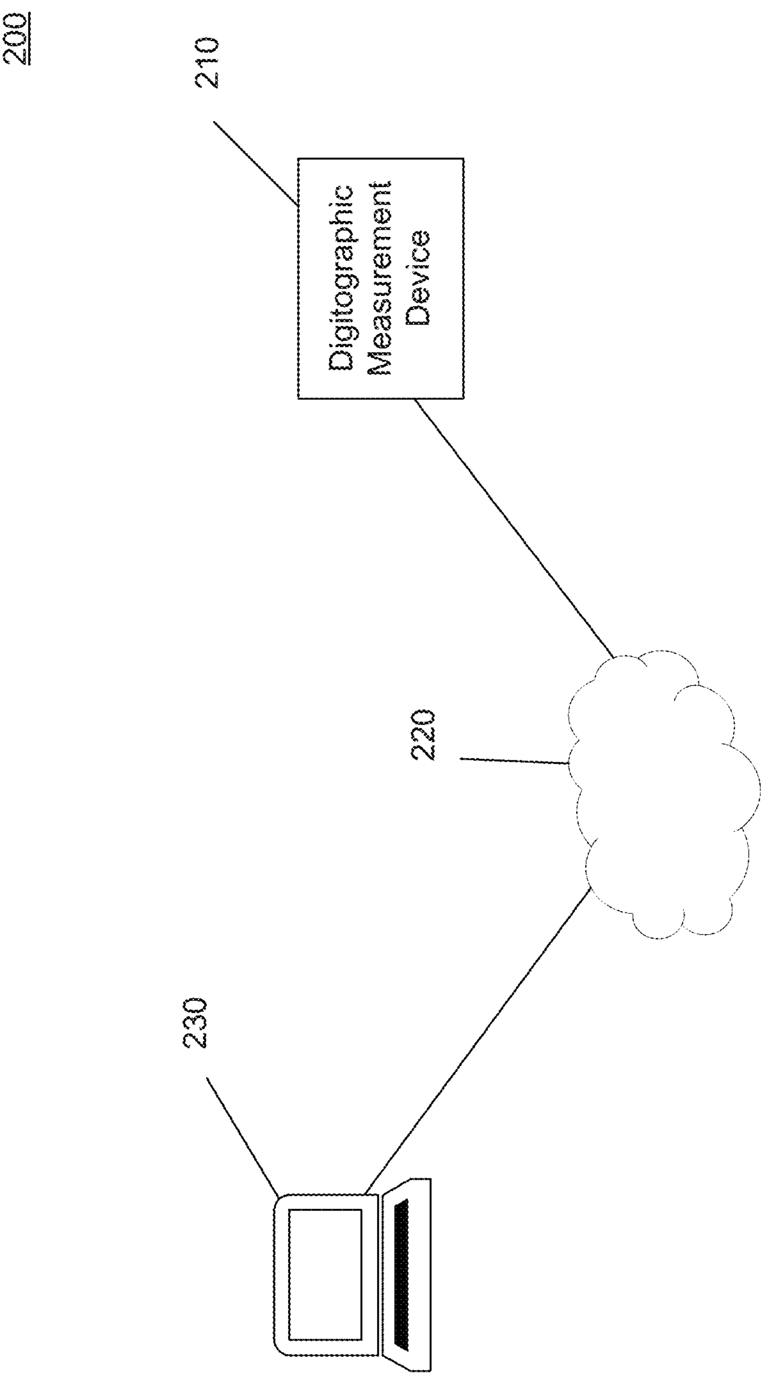
FIG. 2 is a conceptual illustration of a digitographic measurement system in accordance with an embodiment of the invention.

Digitographic measurement systems enable the acquisition and processing and key press data. In many embodiments, digitographic measurement systems include a digitographic measurement device as well as a controller. Controllers can include processing circuitry for enabling the processing of key press data. Turning now to FIG. 2, a system diagram for a digitographic measurement system in accordance with an embodiment of the invention is illustrated.

System 200 includes a digitographic measurement device 210 which is connected via a network 220 to a controller 230. In many embodiments, the network is a wireless network. However, wired connections can be used to connect digitographic measurement devices to controllers. Indeed, in numerous embodiments, digitographic measurement devices have built in controllers with wired connections as part of a single unit. As such, as can be readily appreciated, the network may not be needed as appropriate to the requirements of specific applications of embodiments of the invention.

Figure 3:
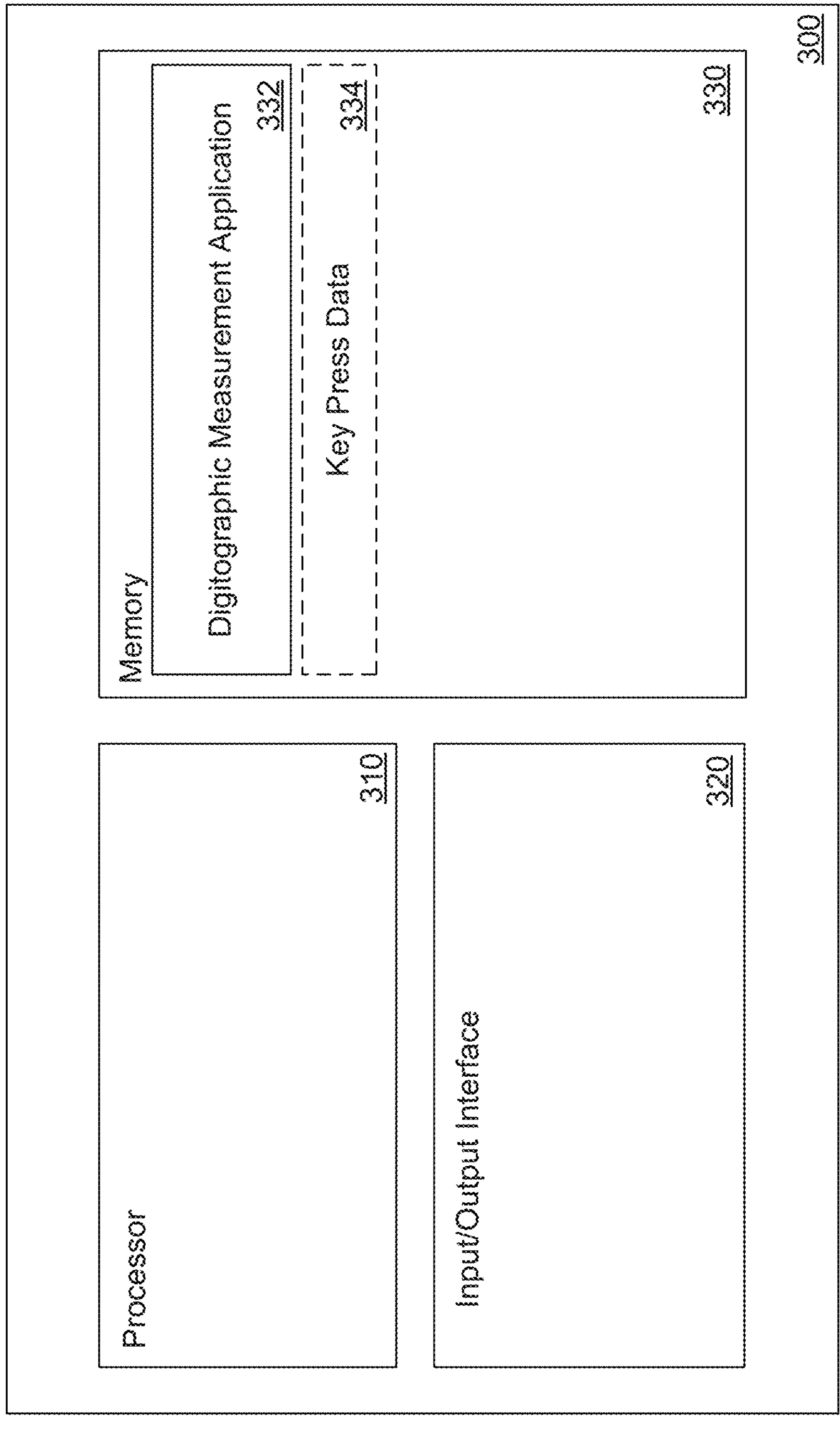
FIG. 3 is a block diagram of a controller in accordance with an embodiment of the invention.

Turning now to FIG. 3, a block diagram for a controller in accordance with an embodiment of the invention is illustrated. Controller 300 includes a processor 310. Processors can be any logic circuitry capable of computing such as, but not limited to, central processing units, graphics processing units, application-specific integrated circuits (ASICs), field-programmable gate arrays (FPGAs), and/or any other logic circuit as appropriate to the requirements of specific applications of embodiments of the invention.

The controller 300 further includes an input/output (I/O) interface 320. In many embodiments, the I/O interface offers connection capability to digitographic measurement devices. The I/O interface can further be used to connect to other devices. For example, in many embodiments, the I/O interface can be used to provide a report based on key press data to a screen or any other storage and/or display device. A memory 330 is further included in the controller 300. The memory can be any type of data storage media including (but not limited to) volatile memory, non-volatile memory, and any mix thereof. The memory 330 stores a digitographic measurement application 332 capable of directing the processor to carry out various digitographic measurement processes which are discussed further below. Key press data 334 can be stored in memory 330 when acquired.

A particular system architecture and controller architecture are illustrated in FIGS. 2 and 3, respectively. However, as can be readily appreciated, any number of different configurations such as (but not limited to) systems using multiple digitographic measurement devices and digitographic measurement devices with incorporated controllers can be utilized without departing from the scope or spirit of the invention. Digitographic measurement processes are described in further detail below.

Digitographic Measurement Processes

Digitographic measurement devices can be used to acquire key press data from users that can objectively indicate whether or not a user presents with cardinal motor symptoms. In many embodiments, the user is instructed to place their index and middle fingers on two keys of a digitographic measurement device and perform approximately thirty seconds of repetitive alternating finger tapping (RAFT). The digitographic measurement device can capture the amplitude of each key independently over time to produce key press data. In many embodiments, the key press data includes a signal from each key in the digitographic measurement device that represents the displacement (i.e. the amplitude) of the key over time. The captured signal for each key can be processed to produce a number of QDG metrics which in turn can indicate the presence of a one or more cardinal motor symptoms.

Figure 4:
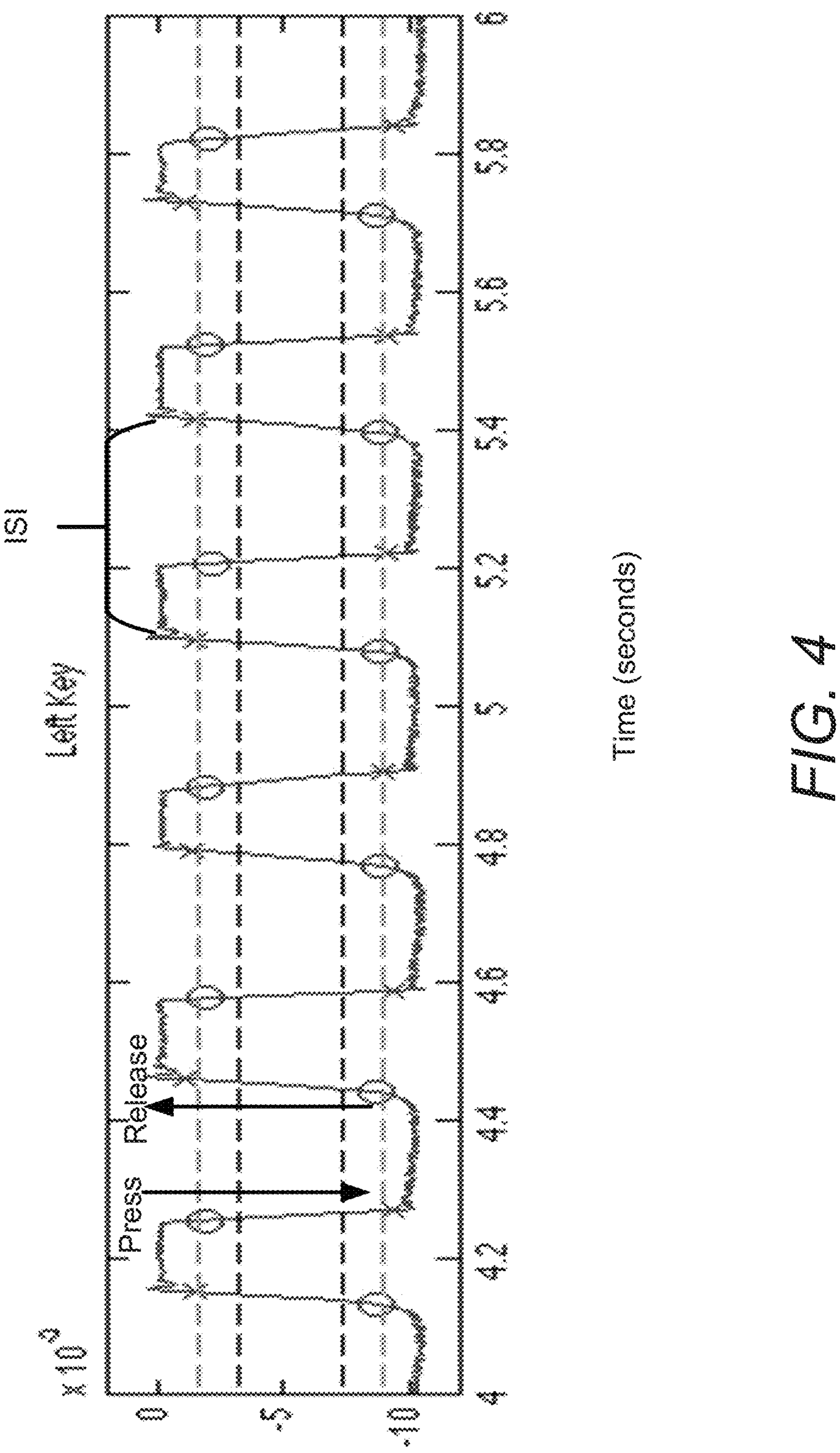
FIG. 4 is an example ideal signal as part of a set of key press data from a healthy patient.

In many embodiments, the QDG metrics include a rigidity metric, a bradykinetic amplitude metric, a bradykinetic frequency metric, a bradykinetic sequence effect metric, a tremor metric, a freeze behavior metric (i.e. arrhythmicity), and a freezing of upper limb (FOUL) metric. An example signal from a single key as actuated by a healthy patient in accordance with an embodiment of the invention is illustrated in FIG. 4. As can be seen, each key press has a press phase and a release phase. While the illustrated signal is healthy and represents well defined key presses, a person presenting with motor symptoms may produce a much less regular signal. A key press can also be referred to as a "strike", and the interstrike interval (ISI) can be understood as the time between two key presses. The morphology of the signal can be used to generate QDG metrics.

The rigidity metric can be understood as the average rate of passive release of a key press. Therefore, the rigidity metric can be calculated by averaging the difference in amplitude between the lowest point of the key press and the highest point of the key release divided by the total time to release the key, for each key release during a test. The inverse of the release speed can be used as the rigidity metric to correspond with the MDS-UPDRS III classification that higher scores indicate increased motor disability; the normative range for the rigidity metric is between 5.88 and 9.09 sec/mm. Higher values tend to indicate worse symptoms.

The bradykinetic amplitude metric can be calculated by averaging the distance between the highest point of a key press and the lowest point of a key press, for each key press during a test. The normative range for the bradykinetic amplitude metric is between 8.30 and 8.88 mm. Lower values tend to indicate worse symptoms.

The bradykinetic frequency metric can be calculated as inverse of the mean interstrike interval (ISI) over the course of a test, where the ISI is the time between two key presses of the same finger. Then normative range for the bradykinetic frequency metric is between 2-4 Hz. Lower values tend to indicate worse symptoms.

The bradykinetic sequence effect metric can be calculated by fitting exponential curves ($y=Ae^{x}$) to quantify the decrement in amplitude over time during a test. The sequence effect can then be quantified by ln(A/abs(x)) where a higher number is indicative of a worse sequence effect. The normative range for the bradykinetic sequence effect metric is between 0.0 and 0.11.

The tremor metric is the percentage of time of the total task time spent in a tremor state. Tremor states can be identified by identifying two consecutive key presses where the ISI is less than 200 ms and the duration of at least one of the key presses is less than 70 ms. However, depending on the implementation of the digitographic measurement device and the condition to be diagnosed, these values can differ. A normative value for tremor (indicating no tremor) is 0%. However, a low percentage that is not reoccurring across tests can be the result of spontaneous error by the user, and can be worth investigating further by a medical professional to determine if tremor is in fact present.

The freeze behavior metric is the coefficient of variation of the ISI (i.e. the standard deviation of the ISI over the mean ISI for the task). The normative range for the freeze behavior metric is 0.07-0.21. Higher values indicate worse symptoms.

The FOUL metric is the percentage of time of the total task spent in a freeze state. Freezing states can be identified when the ISI for between two consecutive key presses is greater than the mean ISI of the preceding key presses+two standard deviations. Alternatively, freezing states can be identified when the amplitude of a key press is 30% or lower than the amplitude of the preceding key press. A normative value for the FOUL metric indicating no symptoms is 0%.

Each metric can be compared against a normative range for the respective metric. If the value for the metric falls outside of the normal range, then a qualified medical doctor can diagnose presence of the cardinal motor symptom associated with the respective metric, which may result in a diagnosis for Parkinson's disease should more than two cardinal symptoms be present. As can be readily appreciated, cardinal motor symptoms can also be symptoms of other conditions, and in this way the digitographic measurements can provide diagnostic support for a wide array of conditions.

Figure 5:
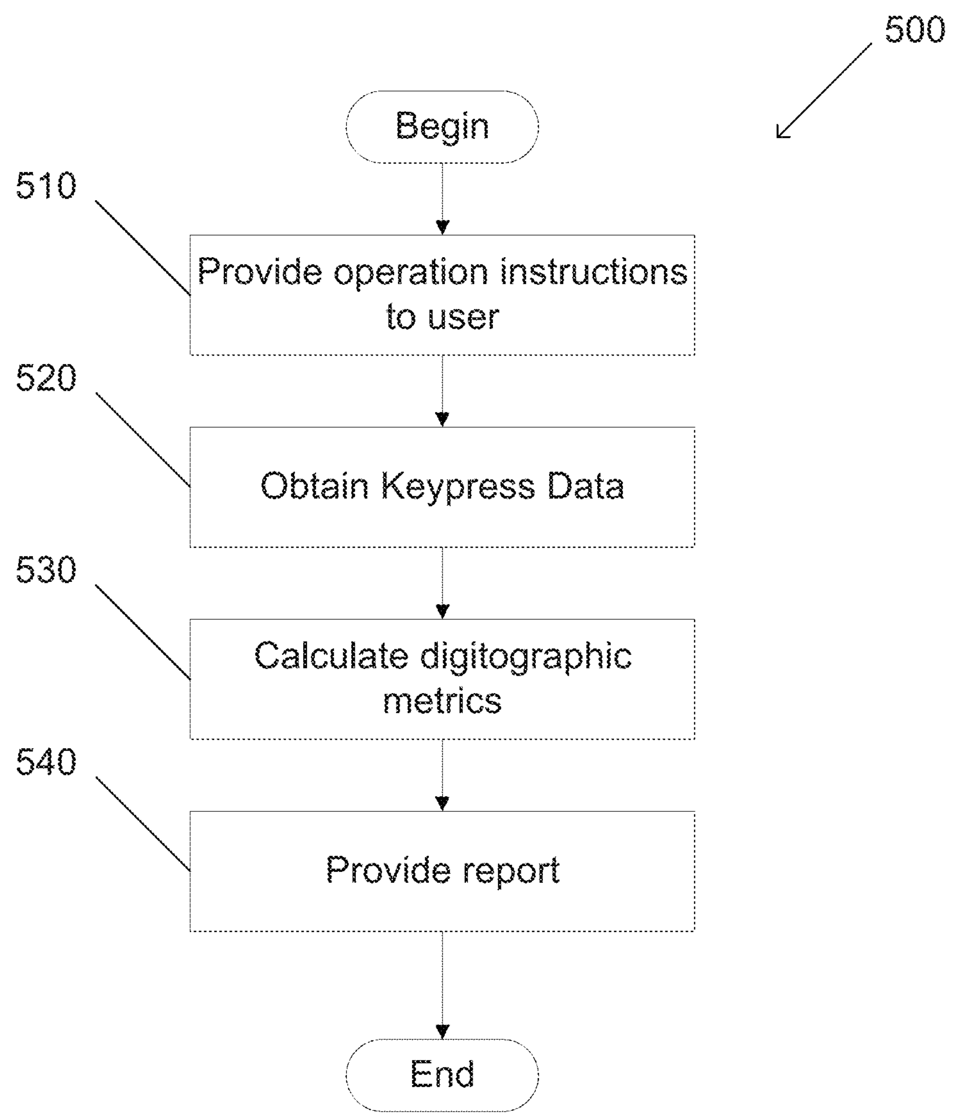
FIG. 5 is a flow chart illustrating a process for the digitographic measurement-based diagnostics in accordance with an embodiment of the invention.
Figure 6:
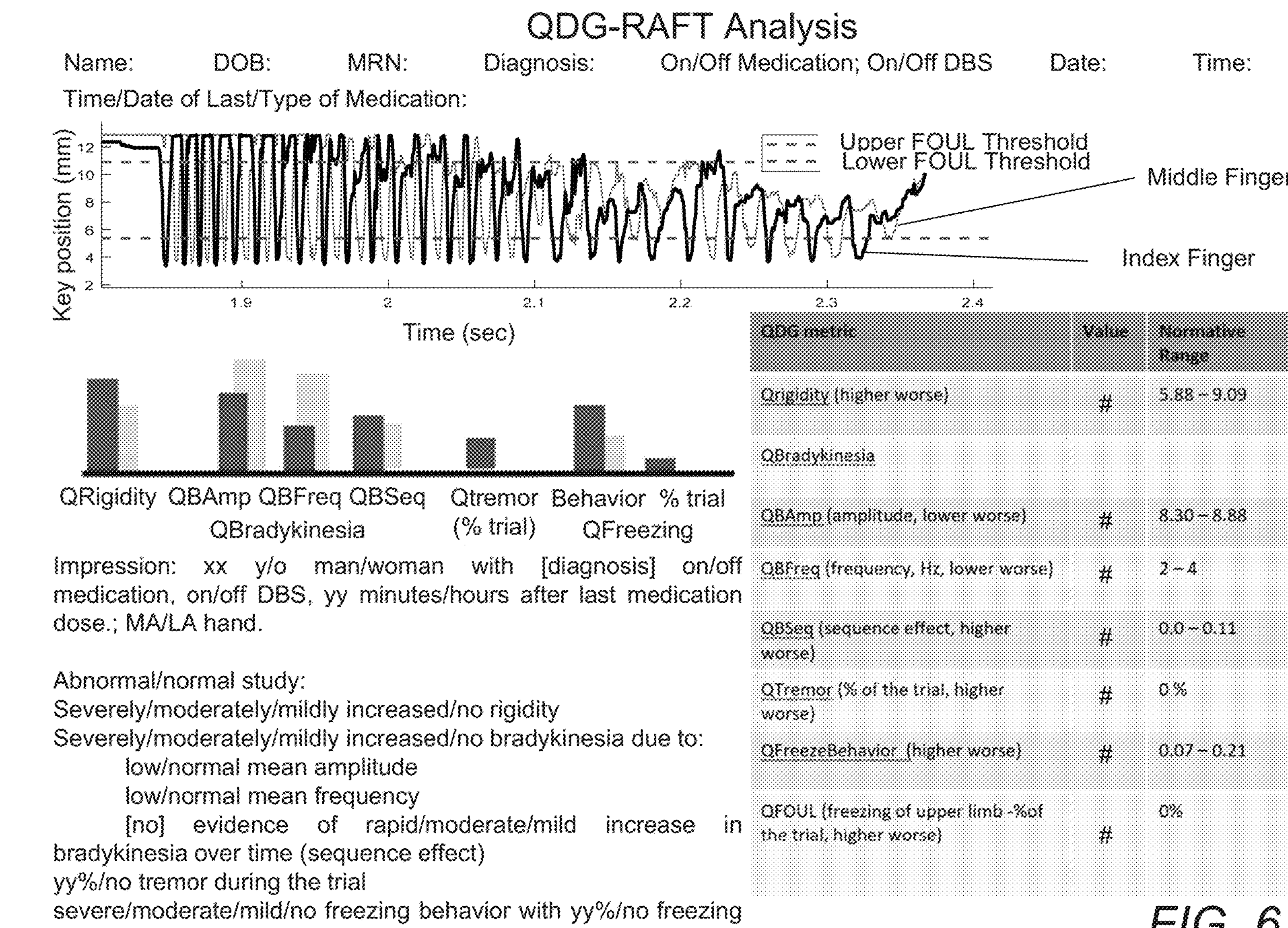
FIG. 6 is an example report generated by a digitographic measurement system in accordance with an embodiment of the invention.

Turning now to FIG. 5, a flow chart for a digitographic measurement process in accordance with an embodiment of the invention is illustrated. Process 500 includes providing (510) operation instructions to a user. In many embodiments, the user is instructed to perform a RAFT test using a digitographic measurement device for a set period from between 10 seconds to 1 minute. However, longer periods can be used in order to acquire more data. Key press data is obtained (520) by the digitographic measurement device describing the key presses over the RAFT test period. The controller calculates (530) QDG metrics based on the key press data, and generates a report (540) that presents the QDG metrics. An example report in accordance with an embodiment of the invention is illustrated in FIG. 6. In many embodiments, the report includes normative ranges. As can be readily appreciated, the particular format of the report can be changed without departing from the scope or spirit of the invention. The report can be used by medical professionals to support a diagnosis.

Although specific systems and methods for digitographic measurement are discussed above, many different systems and methods can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A digitographic measurement device, comprising:

a housing;

a plurality of keys attached to the housing, wherein each key in the plurality of keys is tensioned by a respective spring, wherein the spring tension is set to minimize bounce when the key is released such that passive release of a key is minimally impacted by force from the key striking the bottom of the device;

a plurality of sensors, where each sensor in the plurality of sensors is associated with a key in the plurality of keys and continuously measures key displacement amplitude during a rapid alternating finger tapping test; and an input/output interface within the housing;

where the digitographic measurement device is configured to transmit key press data generated by the sensors to a controller via the input/output interface; and where the key press data is used to generate a plurality of digitographic metrics that describe motor symptoms of a user of the digitographic measurement device, wherein the digitographic metrics are calculated based on a continuous amplitude signal from the key press data to generate a report for clinical diagnosis support, and wherein the digitographic metrics comprise a rigidity metric, wherein the rigidity metric is calculated by averaging the difference in amplitude between a lowest point of a given key press and a highest point of a given key release subsequent to the given key press, for each key press in the key press data.

2. The digitographic measurement device of claim 1, wherein the material of each key minimizes bounce when the key is released.

3. The digitographic measurement device of claim 1, wherein at least one sensor in the plurality of sensors is selected from the group consisting of Hall effect sensors, optical sensors, magnetic encoders, and potentiometers.

4. The digitographic measurement device of claim 1, wherein the digitographic metrics further comprise at least one of: a bradykinetic amplitude metric, a bradykinetic frequency metric, a bradykinetic sequence effect metric, a tremor metric, a freeze behavior metric, and a freezing of upper limb (FOUL) metric.

5. The digitographic measurement device of claim 4, wherein the bradykinetic amplitude metric is calculated by averaging the distance between a highest point of a given key press and a lowest point of a subsequent key press, for each key press in the key press data.

6. The digitographic measurement device of claim 4, wherein the bradykinetic frequency metric is calculated by taking the inverse of the mean of the interstrike interval over the key press data.

7. The digitographic measurement device of claim 4, wherein the bradykinetic sequence effect metric is calculated by fitting at least one exponential curve to quantify a decrement in amplitude over time.

8. The digitographic measurement device of claim 4, wherein the tremor metric is calculated as the percentage of time over the key press data where an interstrike interval between two consecutive key presses is less than 200 ms and the duration of at least one of the two consecutive key presses is less than 70 ms.

9. The digitographic measurement device of claim 4, wherein the freeze behavior metric is the coefficient of variation of an interstrike interval.

10. The digitographic measurement device of claim 4, wherein the FOUL metric is calculated as the percentage of time over the key press data where an interstrike interval between two consecutive key presses is greater than a mean interstrike interval over preceding key presses plus two standard deviations.

11. The digitographic measurement device of claim 4, wherein a digitographic metric outside of a respective normative range indicates presence of a motor symptom.

12. The digitographic measurement device of claim 11, wherein the key press data is further used to generate a report indicating the presence of Parkinson's disease based on digitographic metric values indicating the presence of at least two cardinal motor symptoms of Parkinson's disease.

13. The digitographic measurement device of claim 1, wherein the controller is integrated into the housing.

14. A method for diagnosing motor symptoms, comprising:

providing a digitographic measurement device to a user, wherein the digitographic measurement device comprises:

a housing;

a plurality of keys attached to the housing, wherein each key in the plurality of keys is tensioned by a respective spring, wherein the spring tension is set to minimize bounce when the key is released such that passive release of a key is minimally impacted by force from the key striking the bottom of the device;

performing a rapid alternating finger tapping (RAFT) test using the digitographic measurement device;

recording key press data comprising a continuous amplitude signal describing the key displacement amplitude of each key press over the course of the RAFT test;

calculating a plurality of digitographic metrics based on the key press data; and providing the digitographic metrics and an indication of which motor symptoms the user presents based on the digitographic metrics, wherein the digitographic metrics are calculated based on the continuous amplitude signal to generate a report for clinical diagnosis support, and wherein the digitographic metrics comprise a rigidity metric, wherein the rigidity metric is calculated by averaging the difference in amplitude between a lowest point of a given key press and a highest point of a given key release subsequent to the given key press, for each key press in the key press data.

15. The method of claim 14, wherein the digitographic metrics at least one of: a bradykinetic amplitude metric, a bradykinetic frequency metric, a bradykinetic sequence effect metric, a tremor metric, a freeze behavior metric, and a freezing of upper limb (FOUL) metric.

16. The method for diagnosing motor symptoms of claim 14, further comprising providing an indication that the user presents with Parkinson's disease when the digitographic metrics indicate the presence of at least two cardinal motor symptoms of Parkinson's disease.

17. The method for diagnosing motor symptoms of claim 14, wherein the digitographic measurement device comprises:

a plurality of sensors, where each sensor in the plurality of sensors is associated with a key in the plurality of keys and continuously measures key displacement amplitude during the RAFT test; and an input/output interface within the housing.

18. A digitographic measurement system for measuring motor symptoms, comprising:

a digitographic measurement device, comprising:

a housing;

a plurality of keys attached to the housing, wherein each key in the plurality of keys is tensioned by a respective spring, wherein the spring tension is set to minimize bounce when the key is released such that passive release of a key is minimally impacted by force from the key striking the bottom of the device;

a plurality of sensors, where each sensor in the plurality of sensors is associated with a key in the plurality of keys and continuously measures key displacement amplitude during a rapid alternating finger tapping test; and an input/output interface within the housing;

where the digitographic measurement device is configured to transmit key press data generated by the sensors to a controller via the input/output interface;

the controller, comprising:

a processor; and a memory containing a digitographic measurement application, where the digitographic measurement application directs the processor to:

obtain the key press data from the digitographic measurement device;

calculate a plurality of digitographic metrics that describe motor symptoms of a user of the digitographic measurement device; and provide a report for clinical diagnosis support, the report comprising the plurality of digitographic metrics calculated based on a continuous amplitude signal from the key press data and an indication of the presence of any motor symptoms in a user based on the plurality of digitographic metrics, wherein the digitographic metrics comprise a rigidity metric, wherein the rigidity metric is calculated by averaging the difference in amplitude between a lowest point of a given key press and a highest point of a given key release subsequent to the given key press, for each key press in the key press data.

19. The digitographic measurement system for measuring motor symptoms of claim 18, wherein the controller is integrated into the housing of the digitographic measurement device.

* * * * *